United States Patent [19]

Hansen et al.

[11] Patent Number: 5,763,392
[45] Date of Patent: Jun. 9, 1998

[54] TREATMENT OF DIABETES BY ADMINISTRATION OF MYO-INOSITOL

[76] Inventors: Barbara C. Hansen, 6501 Bright Mountain, Mclean, Va. 22101; Harry L. Greene, 777 S. Flager Dr., West Tower Suite 1400, West Palm Beach, Fla. 33401; Heidi K. Ortmeyer, 2 Craven Crt., Baltimore, Md. 21244

[21] Appl. No.: 648,689

[22] Filed: May 15, 1996

Related U.S. Application Data

[63] Continuation of Ser. No. 173,814, Dec. 22, 1993, abandoned.

[51] Int. Cl.$^6$ .......... A61K 38/00; A01N 43/04; A23L 1/30
[52] U.S. Cl. .......... 514/2; 514/3; 514/52; 514/62; 514/251; 514/725; 514/866; 530/350; 530/399; 530/801; 426/72; 426/74; 426/648; 426/656; 426/658

[58] Field of Search .............. 514/2, 3, 52, 62, 514/251, 725, 866; 530/350, 399; 426/72, 74, 648, 656, 658

[56] References Cited

U.S. PATENT DOCUMENTS

| 4,921,877 | 5/1990 | Cashmere et al. | 514/866 |
| 5,124,360 | 6/1992 | Larner et al. | 514/738 |

OTHER PUBLICATIONS

Arendup et al, *Acta Neurol. Scand*, vol. 80, pp. 99–102, 1989.

*Primary Examiner*—Cecilia J. Tsang
*Assistant Examiner*—Abdel A. Mohamed

[57] ABSTRACT

Method for lowering the plasma glucose levels of diabetics by administering myo-inositol. Also the invention concerns a nutritional composition containing myo-inositol.

18 Claims, 5 Drawing Sheets

TREATMENT OF DIABETES BY ADMINISTRATION OF MYO-INOSITOL

This application is a continuation application of U.S. application Ser. No. 08/173,814, filed Dec. 22, 1993 now abandoned.

FIELD OF THE INVENTION

The present invention concerns treatment of diabetes with myo-inositol and nutritional compositions containing same.

BACKGROUND OF THE INVENTION

Diabetes is a significant disease in humans. Although a complex disease, it is characteristic of subjects having diabetes to have an impaired ability to remove serum or plasma glucose after a glucose load such as after meal ingestion. Such an impairment (sometimes referred to as "glucose intolerance") in severe cases can lead to significant clinical sequelae such as renal failure.

Prior art methods for treating glucose intolerance include the use of insulin or adherence to strict diets which limit intake of easily metabolized carbohydrates. Several liquid enteral formulas designed for use by diabetes patients are commercially available such as Glucerna® nutritional formula (available from Ross Laboratories, Columbus, Ohio). One such enteral formula is described in fructose is part of the carbohydrate component.

Other prior art methods for treating diabetes or glucose intolerance include administration of inositol triphosphate (U.S. Pat. No. 5,023,248) and D-chiro-inositol (U.S. Pat. No. 5,124,360).

Myo-inositol is known in the nutritional field to be an important nutritional component of the diet (see, for example, Holub, B. J., "The Nutritional Significance, Metabolism, and Function of myo-Inositol and Phosphatidylinositol in Health and Disease" in Adv. Nutr. Res. 4:107–141 (1982)). Low levels of myo-inositol are typically added to infant formulas and adult enteral nutritional formulas. In addition, administration of low levels of dietary inositol has been found to have certain other beneficial effects (see, Price, D. E., et al., "Effect of Aldose Reductase Inhibition on Nerve Conduction Velocity and Resistance to Ischemic Conduction Block in Experimental Diabetes," Diabetes, 37:969–973 (1988); Greene, D. A., et al., "Impaired Rat Sciatic Nerve Sodium-Potassium Adenosine Triphosphatase in Acute Streptozocin Diabetes and its Correction by Dietary Myo-Inositol Supplementation," J. Clin. Invest., 72:1058–1063(1983); Knudsen, G. M., et al., "Myo-Inositol Normalizes Decreased Sodium Permeability of the Blood-Brain Barrier In Streptozotocin Diabetes," Neuroscience, 29(3):773–777 (1989); Hallman, M., et al., "Inositol Supplementation In Respiratory Distress syndrome:Relationship Between Serum Concentration, Renal Excretion, and Lung Effluent Phospholipids," The Journal of Pediatrics, 110(4):604–610 (1987); and Greene, D. A., et al., "Effects of Insulin and Dietary Myoinositol on Impaired Peripheral Motor Nerve Conduction Velocity in Acute Streptozotocin Diabetes," The Journal of Clinical Investigation, 55:1326–1336 (1975)). However, myo-inositol has been reported to be without effect for lowering plasma glucose in streptozotocin diabetic rats after a glucose load (Huang, L. C., et al., "Effect of Acute D-Chiroinositol on Plasma Glucose in Diabetic Rats and Non-Diabetic Rats Given a Glucose Load," FASEB, 6(5):A1629, Abstract 4009 (1992)). Furthermore, administration of myo-inositol to patients receiving a high dose (20 g per day) was found not to have any beneficial effects (Arendrup, K., et al., "High-Dose Dietary Myo-Inositol Supplementation Does Not Alter the Ischaemia Phenomenon in Human Diabetes," Acta Neurol Scand, 80:99–102 (1978)).

As hereinafter described, it has been unexpectedly discovered that administration of myo-inositol at high doses is effective in lowering plasma glucose levels of diabetics.

SUMMARY OF THE INVENTION

The present invention is directed to a method for treating diabetes in a human subject in need of treatment comprising orally administering to said subject a nutritional composition comprising protein, lipid and carbohydrate in combination with an effective plasma glucose lowering amount of myo-inositol.

DETAILED DESCRIPTION OF THE INVENTION

In the method of the invention an effective plasma glucose lowering amount of myo-inositol is administered to a subject in need of such treatment. Such subjects are diabetics or patients otherwise manifesting glucose intolerance.

For the purpose of the present invention, the effective amount of myo-inositol to be administered is based on total body mass. Although use of total body mass is more convenient, in some instances it is preferred to use lean body mass because glucose uptake and utilization is primarily a function of lean tissue. Several methods for measuring lean body mass are listed in Modern Nutrition in Health and Disease, Ed. Shils, Olson, Shike, 8th Edition, Lea & Febiger, 1994, pages 783–791. Lean body mass can be estimated in humans by the method described as anthropometry (see Modern Nutrition in Health and Disease, Ed. Shils, Olson, Shike, 8th Edition, Lea & Febiger, 1994, pages 785–786). The anthropometry technique uses various body circumferences and skinfold thickness (really a double layer of skin and subcutaneous tissue, measured with special calipers. Satisfactory calipers are Harpenden Caliper, H. E. Morse Co., Holland, Mich.; Holtain-Harpenden Caliper, Holtain Ltd., Byrnberian, Crymmych, Pembrokeshire, Wales; and Large Caliper, Cambridge Scientific Industries, Inc., Cambridge, Md.). The usual sites for skinfold measurements are the midtriceps region, at the inferior tip of the scapula, and just above the iliac crest. One grasps the tissue between thumb and forefinger, shaking it gently to exclude underlying muscle, and stretching it just far enough to permit the jaws of the spring-activated caliper to impinge on the tissue. Because the jaws compress the tissue, the caliper reading diminishes for a few seconds, and then the dial is read. In subjects-with moderately firm, rather thin subcutaneous tissue the measurement is easy to make; but in those with flabby, easily compressible tissue and in those with very firm tissue not easily deformable, the measurement is more difficult.

Cross-sectional area of the muscle-bone (M+B) and fat components of the arm can be calculated from arm circumference and skinfold thickness at the midpoint, as follows (T is triceps skinfold, B is biceps):

$$(M+B) \text{ area} = \frac{1}{4\pi} \left[ circ. - \frac{\pi}{2} (T+BSF) \right]^2,$$

and by subtraction from total area (circ.$^2$/4 $\pi$) arm fat area.

An effective amount of myo-inositol is about 0.05 to about 5 g per kg of total body mass per day, preferred is about 0.1 to about 5 g per kg of total body mass per day, more preferred is about 0.2 to about 3 g per kg of total body mass per day, and most preferred is about 0.4 g per kg of total body mass per day.

Myo-inositol for the invention can be obtained from various commercial sources, such as Aldrich Chemical Co., Milwaukee, Wis. The method of the invention typically results in lowering the plasma glucose level by at least 8%, preferably about 10% to about 50%.

In the method of the invention the myo-inositol is administered in combination with a nutritional composition comprised of protein, lipid, and carbohydrate. Such compositions are typically normal meals. Thus, the myo-inositol can be taken with a meal, just before a meal, or just after a meal. The myo-inositol can be in the form of a tablet, capsule, dry powder, suspension, solution, etc. A preferred means of administering the myo-inositol is to incorporate the myo-inositol into a nutritional composition which is subsequently consumed by the subject.

Thus, the present invention is also directed to a nutritional composition comprising protein, lipid, carbohydrate, and an effective plasma glucose lowering amount of myo-inositol.

The nutritional composition of the present invention is preferably enteral; that is, it is designed for oral, intragastric, or transpyloric use. It is also preferred that the composition is nutritionally complete. By the term "nutritionally complete" is meant that the composition contains adequate nutrients to sustain healthy human life for extended periods. The composition of the invention may be an infant formula or adult nutritional composition. The composition also can be milk-based, soy-based, or based on other nutrients.

The composition of the invention contains ingredients which are designed to meet the nutritional needs of mammals, especially humans, such as a protein (amino acid) source, a lipid source, and a carbohydrate source. The composition of the invention can be an infant or adult nutritional composition. Typically milk, skim milk, casein, hydrolyzed casein, hydrolyzed whey protein, whey, vegetable protein concentrate (e.g. soy protein isolate), hydrolyzed vegetable protein (e.g. soy), animal oils, vegetable oils, starch, sucrose, lactose and/or corn syrup solids will be added to the composition to supply part or all of the amino acids and/or protein, lipid, and carbohydrate as well as other nutrients such as vitamins and minerals.

The composition of the invention preferably comprises about 7% to about 30% protein, about 20% to about 56% lipid, and about 20% to about 70% total carbohydrate, said percentages being based on the total caloric value of the composition. More preferably, the composition of the invention preferably comprises about 10% to about 15% protein, about 35% to about 45% lipid, and about 38% to about 52% total carbohydrate, said percentages being based on the total caloric value of the composition. Most preferably, the composition of the invention preferably comprises about 12% protein, about 40% lipid, and about 45% total carbohydrate, said percentages being based on the total caloric value of the composition.

The amount of myo-inositol in the composition is typically, about 0.25 to about 25 g per 100 calories (cal) of total composition, preferably about 0.5 to about 25 g per 100 cal of total composition, more preferably about 1 to about 15 g per 100 cal of total composition, most preferably about 2 g per 100 cal of total composition. Since the myo-inositol is a significant amount of the total carbohydrates of the diet, it is an advantage of the invention that fewer calories are required for more easily metabolized carbohydrates such as glucose or sucrose.

Other than myo-inositol, the carbohydrate component of the composition of the invention can be any suitable carbohydrate known in the art to be suitable for use in nutritional compositions. Typical carbohydrates include sucrose, fructose, xylitol, glucose, maltodextrin, lactose, corn syrup, corn syrup solids, rice syrup solids, rice starch, modified corn starch, modified tapioca starch, rice flour, soy flour, and the like. It is preferred that part of the carbohydrate is fiber. Examples of suitable fibers include soy fiber, pectin, oat fiber, pea fiber, guar gum, gum acacia, modified cellulose, and the like. The fiber is assumed to not contribute significantly to the caloric content of the composition since fiber is metabolized by the intestinal flora to a variable extent. Fiber preferably comprises about 0.5% to about 4 g per 100 cal of total composition.

The lipid can be any lipid or fat known in the art to be suitable for use in nutritional compositions. Typical lipid sources include milk fat, safflower oil, canola oil, egg yolk lipid, olive oil, cotton seed oil, coconut oil, palm oil, palm kernel oil, soybean oil, sunflower oil, fish oil and fractions of all above oils derived thereof such as palm olein, medium chain triglycerides (MCT), and esters of fatty acids wherein the fatty acids are, for example, arachidonic acid, linoleic acid, palmitic acid, stearic acid, docosahexaeonic acid, eicosapentaenoic acid, linolenic acid, oleic acid, lauric acid, capric acid, caprylic acid, caproic acid, and the like. High oleic forms of various oils are also contemplated to be useful herein such as high oleic sunflower oil and high oleic safflower oil.

The protein can be any protein and/or amino acid mixture known in the art to be suitable for use in nutritional compositions. Typical protein sources are animal protein, vegetable protein such as soy protein, milk protein such as skim milk protein, whey protein and casein, and amino acids (or salts thereof) such as isoleucine, phenylalanine, leucine, lysine, methionine, threonine, tryptophan, arginine, glutamine, taurine, valine, and the like. A preferred protein source is sodium caseinate or sodium calcium caseinate optionally supplemented with amino acids.

Nutritionally complete compositions contain all vitamins and minerals understood to be essential in the daily diet and these should be present in nutritionally significant amounts. Those skilled in the art appreciate that minimum requirements have been established for certain vitamins and minerals that are known to be necessary for normal physiological function. Practitioners also understand that appropriate additional amounts (overages) of vitamin and mineral ingredients need to be provided to compensate for some loss during processing and storage of such compositions. The composition of the invention preferably contains 100% of the U.S. Recommended Daily Allowance (RDA) in 500 to 3,500 cal of composition, preferably in 500 to 2,000 cal of composition.

To select a specific vitamin or mineral compound to be used in the composition requires consideration of that compound's chemical nature regarding compatibility with the processing and shelf storage.

Examples of minerals, vitamins and other nutrients optionally present in the composition of the invention include vitamin A, vitamin $B_6$, vitamin $B_{12}$, vitamin E, vitamin K, vitamin C, folic acid, thiamine, riboflavin, niacin, biotin, pantothenic acid, choline, calcium, phosphorous, iodine, iron, magnesium, copper, zinc, manganese, chloride, potassium, sodium, beta-carotene, nucleotides, selenium, chromium, molybdenum, and L-carnitine. Minerals are usually added in salt form. In addition to compatibility and stability considerations, the presence and amounts of specific minerals and other vitamins will vary somewhat depending on the intended consumer population.

The composition of the invention also typically contains emulsifiers and/or stabilizers such as lecithin, (e.g., egg or soy), carrageenan, xanthan gum, mono- and diglycerides, guar gum, carboxymethyl cellulose, stearoyl lactylates, succinylated monoglycerides, diacetyl tartaric acid esters of monoglycerides, polyglycerol esters of fatty acids, or any mixture thereof.

Artificial sweeteners could also be added to the present composition to enhance the organoleptic quality of the composition. Examples of artificial sweeteners include saccharine, aspartame, and the like.

The composition of the invention may also optionally contain natural or artificial flavorants or colorants such as vanilla, chocolate, coconut, banana, strawberry flavors.

The osmolality of the liquid composition of the invention (when ready to consume) is typically about 100 to about 1100 mOsm/kg $H_2O$, more typically about 250 to about 700 mOsm/kg $H_2O$.

The composition of the invention can be prepared by use of standard techniques known in the nutritional art, for example by techniques analogous to those disclosed in U.S. Pat. Nos. 4,921,877 and 4,497,800, the disclosures of which are incorporated herein by reference in their entirety. The myo-inositol can be incorporated into the composition as part of the carbohydrate component or added separately after all other ingredients have been added.

The composition of the invention can be sterilized, if desired, by techniques known in the art, for example, heat treatment such as autoclaving or retorting, irradiation, and the like.

The composition of the invention can be packaged in any type of container known in the art to be useful for storing nutritional products such as glass, lined paperboard, plastic, coated metal cans and the like.

The following examples are to further illustrate the invention but should not be interpreted as a limitation thereof.

EXAMPLE 1

Plasma Glucose Lowering Effect of Myo-Inositol in Rhesus Monkeys

Experimental Design

Chronic administration of myo-inositol and D-chiro-inositol (DCI) incorporated into the complete liquid diet.

1. Compound and administration

Dose: 1.5 g/kg total body mass per day of myo-inositol or DCI for three to five days (in three separate meals).

Route of administration: Oral—incorporated into Sustacal liquid diet (a nutritionally complete liquid diet available from Mead Johnson & Co., Evansville, Ind., U.S.A.) to be ingested by the monkeys as their complete daily provision.

Schedule of administration: Predosing: One to three weeks of Sustacal to establish stable intake levels prior to addition of either DCI or myo-inositol to the diet. Dosing: Three to five days of ingestion of Sustacal liquid diet containing DCI or myo-inositol (blind) followed by—one week of Sustacal liquid diet only, then with cross over to three to five days of the alternative agent (given in random order).

Preparation of myo-inositol and DCI compound containing diets: The diets were prepared by careful weighing of doses by weight of the animal and myo-inositol or DCI added to amounts of Sustacal liquid diet calculated to be fully ingested in approximately the first 80% of the food intake for the day (to assure intake of full dose). The research technician was without knowledge of which compound is being added to the diet (wash out period, however, was known due to addition of no agent).

2. Subjects

Rhesus monkeys (Macaca mulatta)—Adult, ages 8 years and over

N=5 monkeys

Monkeys included in this study ranged from hyperinsuliemic with post prandial glycosuria to mildly diabetic. The monkeys are part of a colony maintained by the Obesity, Diabetes and Aging Research Center, University of Maryland. The development of insulin resistance and diabetes in this colony was first described by Hansen, B. C. and Bodkin, N. L. in "Heterogeneity of insulin response: phases leading to type 2 (non-insulin-dependent) diabetes mellitus in the rhesus monkey," *Diabetologia*, 29:713–719 (1986). The monkeys were designated "F", "G", "X", "H" and "D".

3. Outcome measures and effects monitored a) Food intake measurement:
Sustacal was provided in measured quantity and total food intake per 24 hours determined daily.

b) Body weight:
Was obtained weekly by transfer from cage for weighing (accuracy to 1/10 kg).

c) 24 hour urinary glucose:
Determined quantitatively
1) 3 days during the predosing period
2) 3 days during the period dosing DCI and myo-inositol
Urine was collected directly into an iced container and frozen for glucose analysis.

d) Meal tolerance test
A meal tolerance test was administered on the last day of the DCI dosing period, (with DCI in meal), and on the last day of the myo-inositol dosing period, (with myo in meal) and compared to baseline meal tolerance tests (Sustacal liquid diet only) obtained prior to initiation of agent. Monkeys were anesthetized, and intravenous cannulas inserted two hours after completion of the meal (15 mls Sustacal/kg body weight). The same volume of Sustacal liquid diet was given for each of the three tolerance tests. Blood samples were obtained at 120, 150, 180, 210, 240, 270 and 300 minutes following the meal. Plasma analyses included glucose and insulin determinations, glucose and insulin disappearance rates and glucose and insulin responses.

4. Statistical tests

Paired t tests were used to identify significant changes between the DCI dosing values and the myo-inositol dosing values with the baseline value.

5. Results

The results of the study are shown in FIGS. 1–10.

FIGS. 1–4 show the data for plasma insulin in four of the monkeys. As can be seen, administration of myo-inositol results in an even lower production of insulin than the control or administration of D-chiro-inositol.

FIGS. 5–9 show the data for plasma glucose in the five monkeys tested. As can be seen, administration of myo-inositol resulted in substantial lowering of the plasma glucose responses to the Sustacal in the four monkeys with an initial elevation in plasma glucose concentration—even more than administration of D-chiro-inositol. All data points (7 samples from each of the 5 monkeys) during the control period were paired with the data points during myo-inositol and DCI consumption and analyzed. Control values were 135±10 mg/dl compared to myo-inositol values of 103±5 mg/dl ($p<0.0001$).

Figure 1:
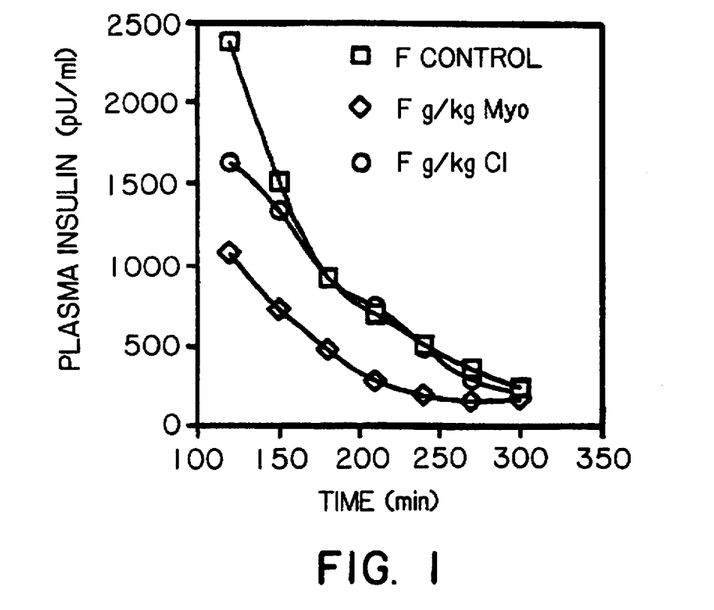
FIG. 1 Plasma insulin vs. time in Monkey F for the study described in Example 1. "Myo" means myo-inositol and "CI" means D-chiro-inositol.
Figure 2:
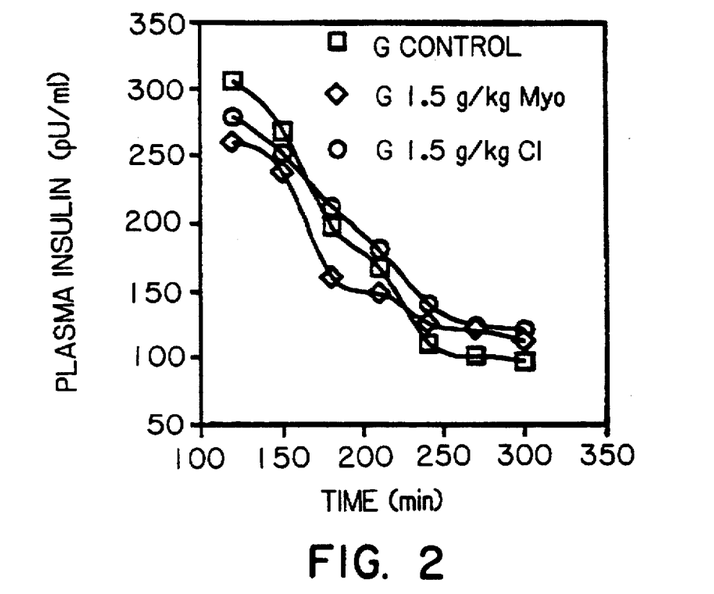
FIG. 2 Plasma insulin vs. time in Monkey G for the study described in Example 1. "Myo" means myo-inositol and "CI" means D-chiro-inositol.
Figure 3:
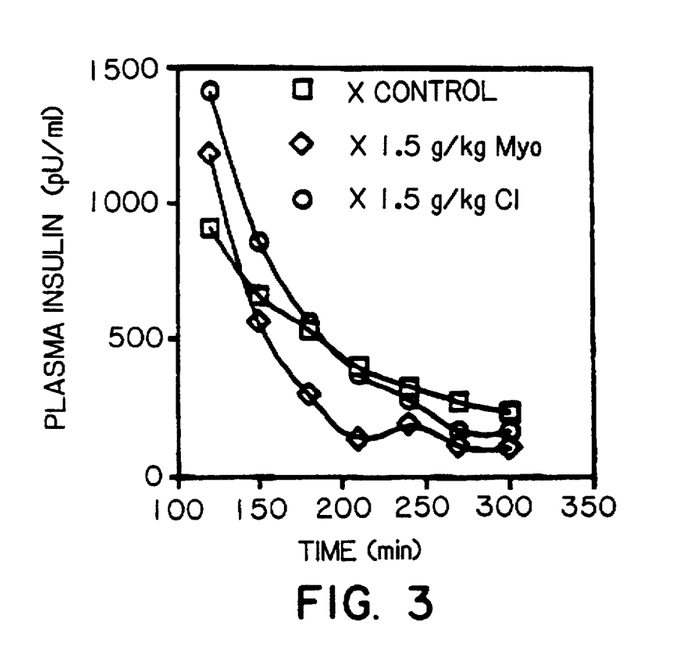
FIG. 3 Plasma glucose vs. time in Monkey X for the study described in Example 1. "Myo" means myo-inositol and "CI" means D-chiro-inositol.
Figure 4:
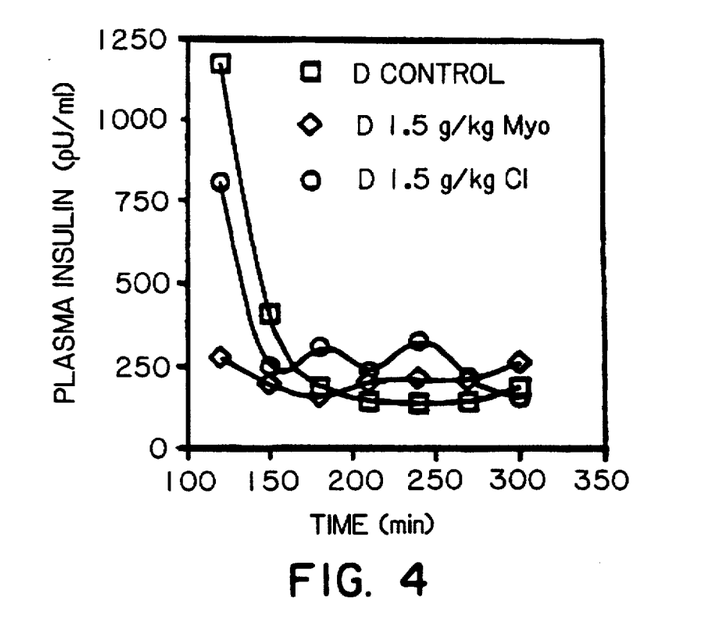
FIG. 4 Plasma glucose vs. time in Monkey D for the study described in Example 1. "Myo" means myo-inositol and "CI" means D-chiro-inositol.
Figure 5:
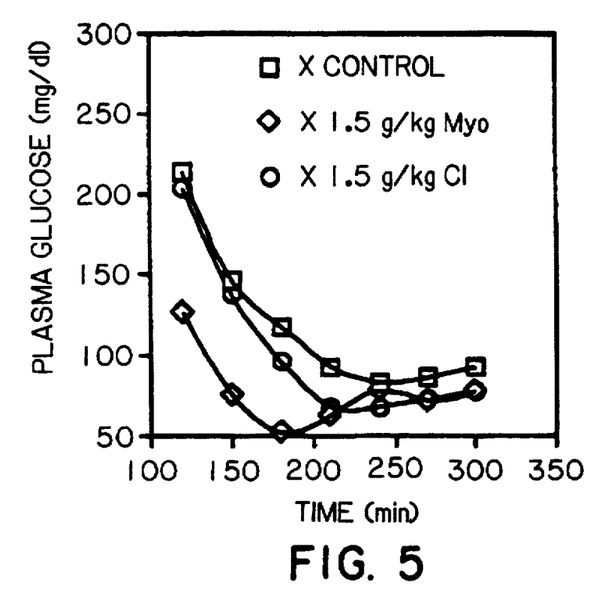
FIG. 5 Plasma glucose vs. time in Monkey X for the study described in Example 1. "Myo" means myo-inositol and "CI" means D-chiro-inositol.
Figure 6:
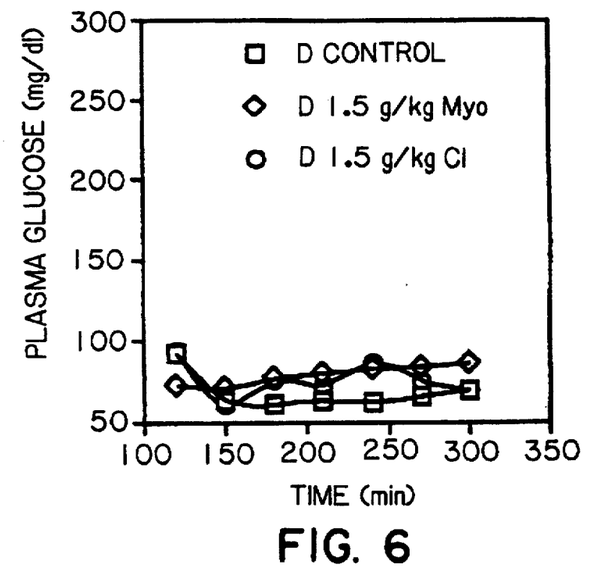
FIG. 6 Plasma glucose vs. time in Monkey D for the study described in Example 1. "Myo" means myo-inositol and "CI" means D-chiro-inositol.
Figure 7:
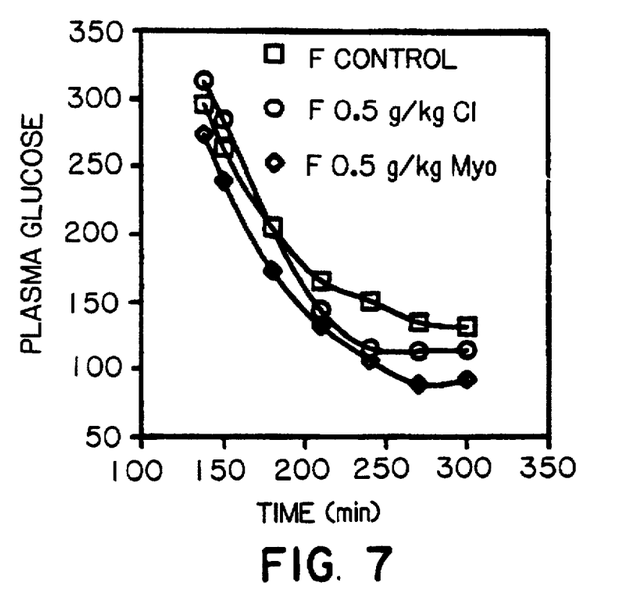
FIG. 7 Plasma glucose vs. time in Monkey F for the study described in Example 1. "Myo" means myo-inositol and "CI" means D-chiro-inositol.
Figure 8:
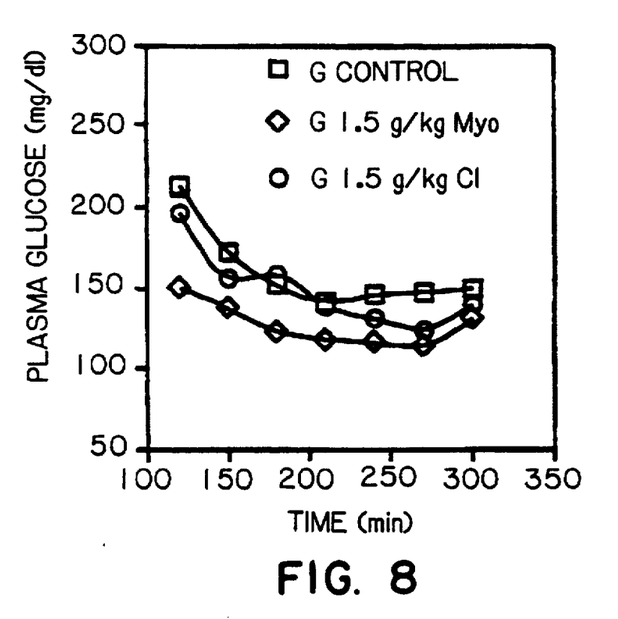
FIG. 8 Plasma glucose vs. time in Monkey G for the study described in Example 1. "Myo" means myo-inositol and "CI" means D-chiro-inositol.
Figure 9:
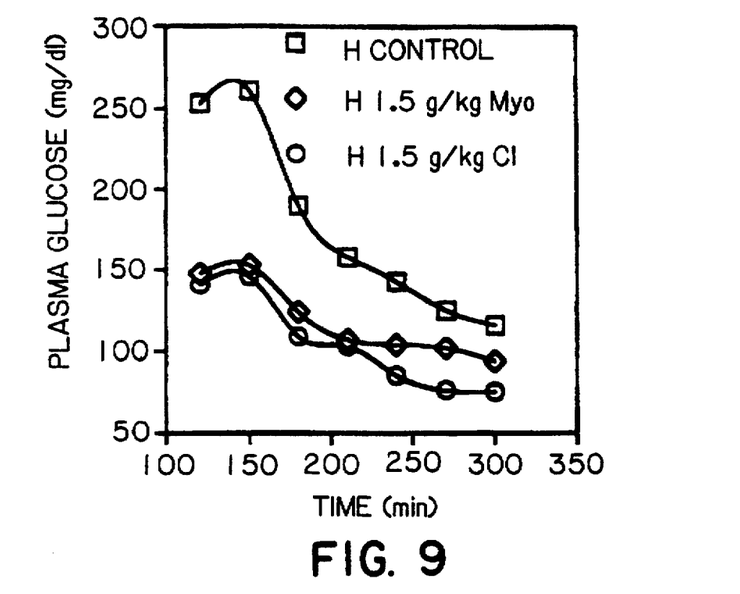
FIG. 9 Plasma glucose vs. time in Monkey H for the study described in Example 1. "Myo" means myo-inositol and "CI" means D-chiro-inositol.
Figure 10:
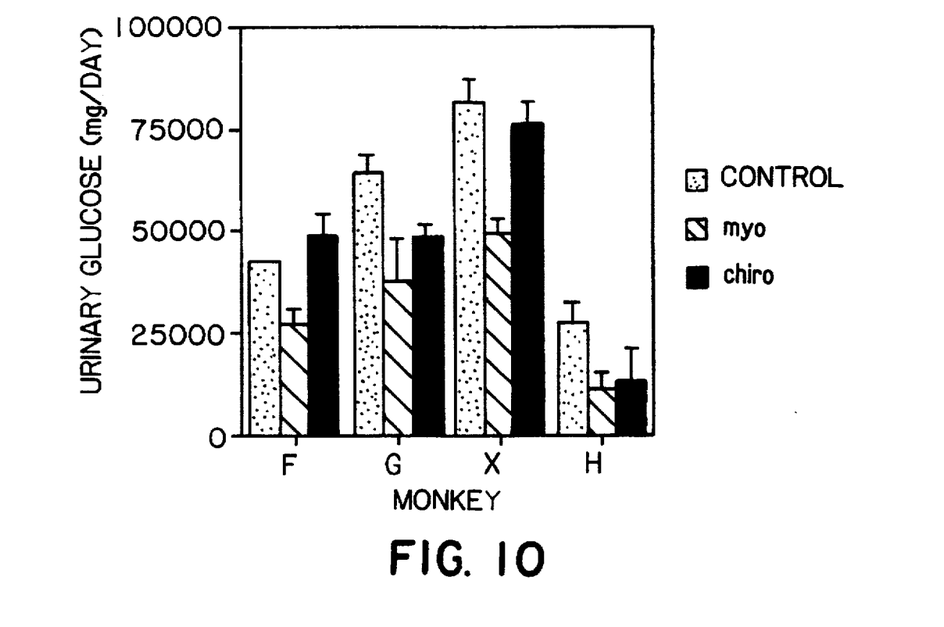
FIG. 10 Urine glucose (mg/day) for each monkey of the study described in Example 1.

FIG. 10 shows the data for urine glucose for four of the five monkeys. Analysis of paired data from all five monkeys showed that mean urine glucose excretion was significantly reduced from 43±14 g/d during the control period to 25±9 g/d during the period of myo-inositol consumption ($p<0.029$). These data are consistent with the plasma glucose and insulin data.

The meal tolerance test was repeated using 0.5 mg/kg total body weight per day of DCI and myo-inositol. Plasma glucose responses were consistent with the data in FIGS. 5–9.

The results of the study demonstrate that myo-inositol was even more effective than DCI in reducing the plasma glucose levels during the single meal tolerance test as well as the urinary excretion of glucose for the three days during which myo-inositol was a component of the diet.

EXAMPLE 2

A typical nutritionally complete enteral composition of the invention has the following formula:

|  | 100 mL |
|---|---|
| Calories | 106 |
| Protein, g | 4.4 |
| Fat, g | 4.5 |
| Carbohydrate*, g | 12.3 |
| Dietary Fiber, g | 1.44 |
| Water, g | 85 |
| Vitamin A, IU | 420 |
| Vitamin D, IU | 34 |
| Vitamin E, IU | 6.3 |
| Vitamin K, µg | 10.6 |

-continued

|  | 100 mL |
|---|---|
| Vitamin C, mg | 2.5 |
| Folic Acid, µg | 34 |
| Thiamine, mg | 0.32 |
| Riboflavin, mg | 0.36 |
| Niacin, mg | 4.2 |
| Vitamin $B_6$, mg | 0.42 |
| Vitamin $B_{12}$ µg | 1.27 |
| Biotin, µg | 25 |
| Pantothenic Acid, mg | 2.1 |
| Choline, mg | 42 |
| Calcium, mg | 85 |
| Phosphorus, mg | 85 |
| Iodine, µg | 12.7 |
| Iron, mg | 1.52 |
| Magnesium, mg | 34 |
| Copper, mg | 0.17 |
| Zinc, mg | 1.69 |
| Manganese, mg | 0.25 |
| Chloride, mg | 144 |
|  | (4.1 mEq) |
| Potassium, mg | 161 |
|  | (4.1 mEq) |
| Sodium, mg | 93 |
|  | (4 mEq) |
| Selenium, µg | 8.5 |
| Chromium, µg | 8.5 |
| Molybdenum, µg | 21 |
| Taurine, mg | 12.7 |
| L-Carnitine, mg | 19 |
| Myo-inositol, g | 12 |

*excluding myo-inositol

The composition has the following caloric distribution:

| Source | % Calories | g/250 Cal (8 fl oz) |
|---|---|---|
| Protein sodium and calcium caseinate | 17 | 10.4 |
| Fat partially hydrogenated soy oil MCT oil | 37 | 10.7 |
| Carbohydrate* | 46 | 29 |

*excluding myo-inositol

I claim:

1. A method for treating diabetes in a human subject comprising orally administering to said subject a human nutritional composition comprising protein, lipid and carbohydrate in combination with an effective plasma glucose lowering amount of myo-inositol of about 0.05 to about 5 g per kg of total body mass per day.

2. The method of claim 1 wherein said effective amount of myo-inositol is about 0.2 to about 3 g per kg of total body mass per day.

3. The method of claim 1 wherein said nutritional composition comprises about 10% to about 15% protein, about 35% to about 45% lipid, and about 38% to about 52% carbohydrate, wherein percentages of said nutritional composition are based on the total caloric value of the composition.

4. The method of claim 1 wherein the plasma glucose level is lowered by at least 8%.

5. The method of claim 1 wherein the plasma glucose level is lowered by about 10% to about 50%.

6. The method of claim 1 further comprising a dietary fiber content of about 0.5 to about 4 g per 100 cal of total composition.

7. The method of claim 1 wherein said nutritional composition comprises about 7% to about 30% protein, about 20% to about 56% lipid, and about 20% to about 70% carbohydrate, wherein percentages of said nutritional composition are based on the total caloric value of the composition.

8. The method of claim 7 wherein the nutritional composition further comprises vitamins and minerals.

9. The method of claim 8 wherein the amount of vitamins and minerals supply 100% of the recommended daily allowance in 500 to 2,500 cal of composition.

10. A nutritional composition comprising protein, lipid, carbohydrate and an effective plasma glucose lowering amount of myo-inositol of about 0.25 to 25 g per 100 cal of total composition.

11. The composition of claim 10 comprising about 7% to about 30% protein, about 20% to about 56% lipid, and about 20% to about 70% total carbohydrate, wherein percentages of said composition are based on the total caloric value of the composition.

12. The composition of claim 10 further comprising dietary fiber content of about 0.5 to about 4 g per 100 cal of total composition.

13. The composition of claim 10 wherein said effective blood glucose lowering amount of myo-inositol is about 1 to about 15 g per 100 cal of total composition.

14. The composition of claim 13 comprising about 10% to about 15% protein, about 35% to about 45% lipid, and about 38% to about 52% total carbohydrate, wherein percentages of said composition are based on the total caloric value of the composition.

15. The composition of claim 13 comprising about 12% protein, about 40% lipid, and about 45% total carbohydrate, said percentages being based on the total caloric value of the composition.

16. The composition of claim 10 further comprising vitamins and minerals.

17. The composition of claim 16 wherein the amount of vitamins and minerals supply 100% of the recommended daily allowance in 500 to 2,000 cal of composition.

18. The composition of claim 17 further comprising at least one of the following components: chromium, selenium, molybdenum, carnitine, taurine, beta-carotene, one or more artificial sweeteners, one or more emulsifiers, or one or more stabilizers.

* * * * *

UNITED STATES PATENT AND TRADEMARK OFFICE
CERTIFICATE OF CORRECTION

PATENT NO  : 5,763,392
DATED      : June 9, 1998
INVENTOR(S) : Barbara C. Hansen, Harry L. Greene, Heidi Ortmeyer It is certified that error appears in the above-identified patent and that said Letters Patent is hereby corrected as shown below:

On the title Page, Item [73] should read as follows:

Assignee:    The University of Maryland, Baltimore. Baltimore, MD

Signed and Sealed this

Twenty-ninth Day of December, 1998

Attest:

BRUCE LEHMAN

Attesting Officer

Commissioner of Patents and Trademarks